United States Patent [19]
Dellon et al.

[11] Patent Number: 5,147,399
[45] Date of Patent: Sep. 15, 1992

[54] METHOD OF TREATING NERVE DEFECTS THROUGH USE OF A BIOABSORBABLE SURGICAL DEVICE

[76] Inventors: Arnold L. Dellon, 3901 Greenspring Ave., Suite 104, Baltimore, Md. 21211; Susan E. Mackinnon, 293 Forest Hill Rd., Toronto, Canada, M5P 2N7

[21] Appl. No.: 664,448

[22] Filed: Feb. 28, 1991

Related U.S. Application Data

[63] Continuation of Ser. No. 150,593, Feb. 1, 1988, abandoned.

[51] Int. Cl.$^5$ ................................. A61F 2/04
[52] U.S. Cl. ....................... 623/12; 623/66; 606/152; 606/153; 606/154
[58] Field of Search ............ 623/12, 14; 606/152, 606/153, 154, 155

[56] References Cited

U.S. PATENT DOCUMENTS

| | | | |
|---|---|---|---|
| 3,044,497 | 7/1962 | Rebut | 606/152 |
| 3,463,158 | 8/1969 | Schmitt et al. | 128/334 R |
| 4,662,884 | 5/1987 | Stensaas | 623/12 |
| 4,759,764 | 7/1988 | Fawcett et al. | 623/66 X |
| 4,870,966 | 10/1989 | Dellon et al. | 606/154 |

OTHER PUBLICATIONS

B. R. Seckel et al., "Nerve Regeneration Through Synthetic Biodegradable Nerve Guides", *J. Plastic Reconstr. Surg.* 74 173-181 (1984).

S. E. Mackinnon et al., "Nerve Regeneration Through a Psuedosynovial Sheath in a Primate Model", *Plastic and Reconstr. Surg.* 75 883-839 (1985).

*Primary Examiner*—David Isabella
*Assistant Examiner*—Debra S. Brittingham
*Attorney, Agent, or Firm*—Vorys, Sater, Seymour and Pease

[57] ABSTRACT

A method of using a bioabsorbable tube device for the repair of nerve defects or gaps comprising the steps of selecting a flexible, porous, bioabsorbable tube device and, then, suturing the nerve ends within the tube device such that a predetermined gap is left between the proximal and distal nerve ends to allow for nerve axon growth across the nerve gap from the proximal nerve end to the distal nerve end.

15 Claims, 2 Drawing Sheets

METHOD OF TREATING NERVE DEFECTS THROUGH USE OF A BIOABSORBABLE SURGICAL DEVICE

This is a continuation of co-pending application Ser. No. 07/150,593 filed on Feb. 1, 1988, now abandoned.

CROSS REFERENCE TO RELATED PATENT

The present application is related to applicants' U.S. Pat. No. 4,870,966 issued Oct. 3, 1989, entitled "Bioabsorbable Surgical Device for Treating Nerve Defects".

BACKGROUND OF THE INVENTION

1. Technical Field

This invention relates generally to methods of treating nerve gaps or defects and, particularly, to a method of using a bioabsorbable surgical device for spanning a significant nerve gap where the nerve ends may not be easily pulled and sutured together.

2. The Prior Art

When a nerve is lacerated or severed it may be repaired by a common surgical procedure known as nerve repair or, technically, neurorrhaphy. With the aid of microsurgical techniques, direct nerve suture can easily be done without the use of additional devices when there is no nerve missing between the severed or lacerated nerve endings. However, when a portion of the nerve is missing, a nerve gap or nerve defect exists. This situation may be overcome by mobilizing the nerve ends, bringing them together and suturing them if the gap or defect is less than 1.5 centimeters. Fairly good results have been obtained by suturing the nerve ends together in this fashion. However, problems do still exist. The process of direct suturing is limited because it is extremely tedious and time consuming. The use of numerous sutures can cause trauma to the nerve which stimulates the formation of intraneural and extraneural connective tissue, or scar tissue. Invasion of the repair site by connective tissue can prevent the regenerating axons in the proximal stump from entering the microscopic tubules contained in the distal stump. This situation often causes formation of painful neuromas at the suture or nerve graft site. Furthermore, it has been shown that for defects or gaps greater then 1.5 centimeters, stretching the nerve ends and directly suturing the ends together creates tension at the suture line which causes greater scar formation and, thus providing poor results.

The technique used to treat nerve gaps is termed "nerve grafting". Typically, the nerve graft material is taken from another part of a person's body, generally a nerve that goes to a sensory area of a lower extremity, such as the sural nerve. The sural nerve is taken from the donor site leaving an area of numbness in the lateral aspect of the patient's foot, a long scar up the patient's leg and the future potential for pain at the site at which the sural nerve graft was taken. It would be desirable to be able to provide a nerve graft material that could provide for nerve growth across a significant nerve gap or defect without using nerve graft material taken from the patient's own body.

Animal (non-human) nerve graft substitutes have also been utilized to provide the necessary spanning of the nerve gap or defect. These nerve heterografts have been sutured to the nerve ends in the same fashion as a human graft. However, these types of substitute nerve grafts suffer from many drawbacks. First, the chances for success in achieving nerve regeneration using such grafts has been extremely unpredictable. Second, there is the potential for an autoimmune response by the body to the foreign nerve graft material.

Recognition of this problem has prompted many researchers to explore alternatives to direct suturing and the use of nerve grafts in bridging nerve gaps or defects and a variety of approaches involving the use of many different types of materials have been experimented with over the past years. Methods and devices have been developed which use both suturing and nonsuturing methods to provide a direct connection between the nerve ends. All of these alternatives seek to protect the anastomotic nerve site by wrapping, tubulizing, or otherwise encasing it with a natural or foreign substance, either absorbable or nonabsorbable. However, none of the prior art references disclose a successful device and method which allows a nerve to regrow across a significant nerve gap without the use of a nerve graft or direct nerve end to nerve end suture line.

U.S. Pat. Nos. 4,534,349 and 4,669,474 both to T. H. Barrows disclose a medical device and method of use for the sutureless repair of lacerated, severed, or grafted nerves. The device is a longitudinally-openable, porous, rough-surfaced tube of a molded natural or synthetic absorbable polymer. This device was not designed for the treatment of nerve gaps. It was designed to repair a broken nerve without the use of sutures by approximating the two nerve ends together and holding them together within a rough-surfaced tube. If used in a situation involving a nerve gap, an autogenous nerve graft would be used. The tubular device would encase both the graft and the two nerve ends or two separate devices would be required one at each end of the graft and respective nerve end. Furthermore, the Barrows molded tube comes in two parts which are then hooked together such that the tube would be fairly rigid which would not permit it to be used in situations where the repaired nerve would be required to go around a corner or be subject to bending forces.

Sutureless tubulization techniques are known to be successful only in the case of very small, single fascicle nerves. The saphenous nerve in rats (0.3–0.5 mm diameter) was transected and repaired with a preformed tube or single leaf of collagen membrane as disclosed by J. M. Rosen, E. N. Kaplan, D. L. Jewett, and J. R. Daniels, "Fascicular Sutureless and Suture Repair of the Peripheral Nerves, A Comparison Study in Laboratory Animals", *Orthopaedic Review* 8 (4), 85 (1979). This method of repair avoids sutures but requires a totally tensionless situation to avoid retraction of the nerve stumps. J. M. Rosen in *Orthopedic Transactions* 6(1), 75(1982) reports that the peroneal nerve in rats (0.5–1.2 mm in diameter) was transected and repaired with a thin-walled, extruded tube of polyglycolic acid, cut open longitudinally along one wall. This method also requires a totally tensionless situation and is not advisable in the case of larger nerves since the tight fit required to maintain adequate nerve stump approximation would not provide for the release of pressure created by post-surgical swelling.

U.S. Pat. No. 4,662,884 to L. J. Stensaas, et al. discloses a very similar method of nerve repair (no gap) using a nonabsorbable silicone rubber. The use of silicone rubber as a tube conduit for nerve repair is also not without its disadvantages. Since the rubber is nonabsorbable in the human body, it will be necessary to perform a second operation to remove the rubber tube after the nerve ends have regrown together. Silicone rubber has the further disadvantage of being impermeable. See, also, R. D. Midgley, et al. "Silicone Rubber Sheathing as an AdJuncta to Neural Anastomosis", *Surgical Clinic of North America,* 48, 1149 (1968), where they report the use of a silicone rubber tube to accomplish nerve repair (no gap) in dogs.

There have been many experiments performed on regrowing nerves across small or insignificant (less than 1.5 centimeters) nerve gaps or defects. Hakan Molander, et al., "Regeneration of Peripheral Nerve Through A Polyglactin Tube", *Muscle and Nerve,* 5:54–57(1982), reported satisfactory results in bridging small nerve gaps (7 to 9 mm in length) by use of a biodegradable polyglactin suture mesh shaped as a tube around the nerve defect as a framework for proliferating cells. Molander, et al. further reported in "Nerve Repair Using a Polyglactin Tube And Nerve Graft: An Experimental Study in the Rabbit", *BIOMATERIALS* 4: 276–280 (1983), that a method of bridging a small nerve gap (10 mm in length) with a polyglactin mesh-tube gave results essentially no different from a conventional nerve graft. However, Molander was using his tube only on small or insignificant nerve gaps (less than or equal to 1 cm).

There is also extensive literature reporting on the use of collagen tubes with or without a lamining gel to treat nerve defects as disclosed by D. G. Kline and G. J. Hayes, "The Use Of A Resorbable Wrapper For Peripheral Nerve Repair, Experimental Studies In Chimpanzees", *J. Neurosurgery,* 121, 737 (1946), and by R. Madison, et al., "Increased Role of Peripheral Nerve Regeneration Using Bioabsorbable Nerve Guides In a Lamining-containing Gel, *Experimental Neurology, 88:* 767–772 (1985). However, with the use of collagen tubes or tubes containing lamining to promote neural growth, it is noted that collagen and lamining are highly immunogenic and that techniques have not been perfected to allow their use in humans without an immune response developing. Furthermore, all of these researchers were using their devices on clinically insignificant gaps of 1 centimeter (cm) or less on lower animal forms and not in primates.

Some researchers have found that nerves will not regenerate across a nerve gap of greater than 10 mm (1 cm). B. R. Seckel, et al., "Nerve Regeneration Through Synthetic Biodegradable Nerve Guides: Regulation by the Target Organ", *J. Plast. Reconstr. Surg.* 74: 173–181 (1984), reported that in a rat model a nerve gap distance of less than 10 mm (1 cm) is crucial to obtain nerve regeneration across a nerve gap or defect.

However, it has been determined through discoveries made by the present inventors that nerves can regenerate across a significant nerve gap greater than 1 cm. S. E. Mackinnon, A. L. Dellon, et al., "Nerve Regeneration Through a Pseudosynovial Sheath in a Primate Model", *Plastic And Reconstructive Surgery,* 75: 833–839 (1985), report that the nerve endings in a baboon grew back together over a 3 cm nerve gap through a vascularized pseudosynovial sheath. The pseudosynovial sheath had been grown in the baboon's own body for a six-week period before use on the baboon's severed ulnar nerve. For this to work in a human it would still be necessary to prepare the sheath in the human body before undertaking repair of the nerve defect. This would require at least two operations and include all of the pain and costs associated with two surgical operations. Therefore, it would be highly desirable to develop a synthetic bioabsorbable nerve conduit that could be used in humans to span significant nerve gaps or defects of 1.5 centimeter or greater.

U.S. Pat. No. 3,937,223 to R. W. Roth teaches a partially-compressed, heat-embossed, flexible, tissue-absorbable, compacted, surgical hemostatic felt having specific fiber and density measurements which is in the form of a thin conformable mat. Two related patents U.S. Pat. Nos. 4,033,938 and 3,960,152, disclose bioabsorbable polymers of unsymmetrically substituted 1,4-dioxane-2,5-diones which are broadly stated in col. 9, lines 29–31 and in the bridging paragraph of cols. 9 and 10 ('938) and in col. 9, lines 20–23 and lines 51–65 ('152) to be useful as tubes or sheets for surgical repair such as nerve and tendon splicing. A similar disclosure in U.S. Pat. No. 4,074,366 to Capozza Col. 6, lines 13–16 and 43–57, relates to poly(N-acetyl-D-glucosamine), i.e. chitin. However, there is no enabling disclosure in the specifications or in their Examples as to how such tubes are to be prepared, the characteristics required, or their method of use.

SUMMARY OF THE INVENTION

It is a primary object of the invention to provide a method of using a flexible, bioabsorbable, tube device that can provide an optimum environment for nerve regeneration across large or significant nerve gaps of from about 2 millimeters to about 6 centimeters.

Another object of the present invention is to provide a method of using a flexible tube device manufactured from a synthetic bioabsorbable material such as those listed in Table I, below, for use as a nerve regeneration conduit.

A further object of the present invention is to provide a method of using a knitted or woven tube manufactured from a synthetic bioabsorbable fiber which is flexible enough to be bent through an arc of 180 degrees without pinching or crimping of the internal diameter of the tube device.

Yet another object of the present invention is to provide a method of using a bioabsorbable, flexible, knitted or woven tube having a corrugated exterior and a relatively smooth-surfaced interior so as to promote nerve axon growth within the tube device.

And, still another object of the present invention is to provide a method of using a flexible, bioabsorbable, nerve tube device which is tissue compatible, minimizes neuroma formation, accommodates post-surgical swelling and provides an optimum environment which is nonimmunogeni for nerve regeneration across a significant nerve gap or defect.

Still other objects and advantages of the invention will in part be obvious and will in part be apparent from the specification.

The present invention provides a method of using a device for the repair of nerve defects or gaps of one and one half centimeters or larger comprising a flexible, porous, knitted or woven mesh tube of a bioabsorbable polymer such as those listed in Table I below. The knitted or woven mesh structure is preferred because it provides a readily flexible structure having the right porosity to provide an excellent environment for nerve regeneration within the device and at the same time permit oxygen diffusion into the environment. Preferably, the tube device is crimped along its exterior to provide a tube which can be bent through an arc of 180 degrees without pinching or crimping the internal circumference of the tube device. The internal surface of the tube is relatively smooth to provide an optimum environment for longitudinal nerve axon growth within the tube device. The internal tube surface is provided with a plurality of flats to provide a tube device having a relatively constant internal diameter. It is undesirable to provide a rough internal surface which may cause the nerve axons to regenerate in an irregular non-longitudinal fashion within the tube device.

TABLE I (1) Poly-alpha-hydroxy acids such as polyglycolic acid (hereinafter PGA), polylactic acid, copolymers of lactic and glycolic acids, and said polymers copolymerized with other polyesters such as epsilon-caprolactone (i.e., U.S. Pat. No. 4,118,470).

(2) Copolymers having a glycolic acid ester and trimethylene carbonate linkages (U.S. Pat. No. 4,243,775), e.g. the copolymer in the MAXON TM (American Cyanamid Company, Wayne, N.J. 07470, USA) suture.

(3) Polydioxanone (U.S. Pat. No. 4,052,988).

(4) Polyesters formed from diols and succinic and/or oxalic acid such as U.S. Pat. Nos. 4,032,993 and 3,883,901, isomorphic copolyoxalates (U.S. Pat. No. 4,141,087), and poly(alkylene oxalates) (U.S. Pat. No. 4,140,678).

(5) Polymers made from unsymmetrically-substituted 1,4-dioxane-2,5-diones (U.S. Pat. No. 3,960,152).

In one embodiment of this invention the knitted or woven mesh tube is manufactured from 100 percent PGA. The PGA material is a bioabsorbable polymer which maintains its tensile strength for approximately thirty days and then is hydrolyzed slowly within the body. The known accepted rate of neural regeneration is approximately one millimeter (1 mm) per day. Therefore a tube device manufactured from a PGA polymer would remain in place long enough to allow a nerve to regenerate across a 30 mm or 3 cm nerve gap or defect.

In another embodiment of the invention the knitted or woven mesh tube is manufactured from a copolymer of glycolide and trimethylene carbonate linkages (MAXON TM suture material). This copolymer is known to maintain its tensile strength for at least fifty-six days and is then resorbed slowly in the body. A tube device manufactured from MAXON TM copolymer fibers could be used to span nerve gaps or defects of 5 centimeters or more.

The use of a corrugated tube device which can be used in the method of this invention for spanning significant nerve gaps or defects comprises selecting a device which is a flexible, porous, bioabsorbable tube device having a corrugated exterior surface and a relatively smooth interior surface, placing a small microsuture through a first end of the tube device and then, through the epineurium layer of a proximal end of the severed nerve, pulling and affixing the proximal nerve ending into the first end of the tube device, placing the second microsuture through a second end of the tube device and then through the epineurium layer of a distal end of the severed nerve, pulling and affixing the distal nerve end into the second end of the tube device, allowing the proximal and distal nerve ends to be spaced sufficiently apart such that the proximal nerve axon will regrow across the nerve gap into the distal nerve end.

BRIEF DESCRIPTION OF THE DRAWINGS

The invention is illustrated by way of example in the accompanying drawings which form part of the specification and in which:

FIG. 6 is a view of a vacuum oven where the collapsed tube and crimping fixture are heated under a vacuum to heat set the externally crimped surface of the tube and FIG. 7 is an enlarged cross-sectional view of the tube device taken along line 7—7 of FIG. 3 showing one embodiment of the woven thread construction to the tube device.

DESCRIPTION OF THE PREFERRED EMBODIMENTS

The method of the present invention utilizes bioabsorbable devices which are flexible tubes made by either the knitting or weaving of bioabsorbable fibers into the shape of a tube and, then, dry heat setting of the tubes to improve the in-vivo strength of the polymer fibers and preferably providing a tube with corrugations along its external surface. The preferable corrugated external tube surface allows for bending of the tube without compromising the internal passageway of the tube device. The tube is used for spanning a significant nerve gap or defect such as occurs when a nerve is severed or lacerated and the nerve ends may not be easily brought back together. The tube is provided with a relatively smooth interior surface to ease insertion of the nerve ends into the tube device and to provide an environment within the tube to promote longitudinal axon growth across the nerve gap or defect.

Figure 1:
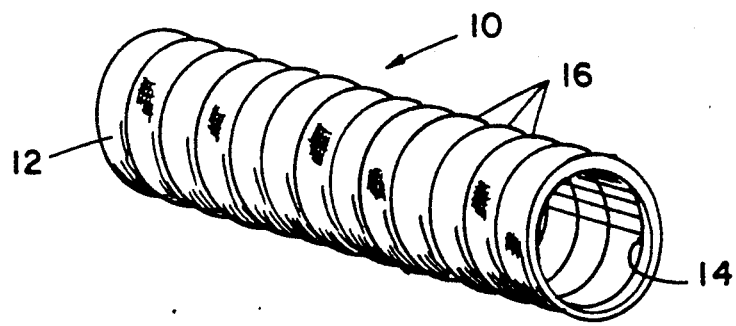
FIG. 1 is a perspective view of the crimped tubular device in accordance with the present invention.

Referring to the accompanying drawings, FIG. 1 shows a bioabsorbable tube device 10 made in accordance with the present invention. The tube 10 has an exterior surface 12 and interior surface 14. The exterior tube surface 12 is shown having a plurality of crimps or corrugations 16, thereon. The corrugations 16 on the exterior tube surface 12 allow the tube device to be bent through an arc of 180 degrees without the pinching or crimping of the internal surface 14. This feature is extremely important to the functioning of the tube device because frequently it is necessary for the tube device to pass over joints or areas where bending of the regenerating nerve will occur. If the interior surface 14 buckles or crimps, the flow of axonal substances across the nerve gap will be blocked and the nerve will not fully regenerate across the gap.

Figure 2:
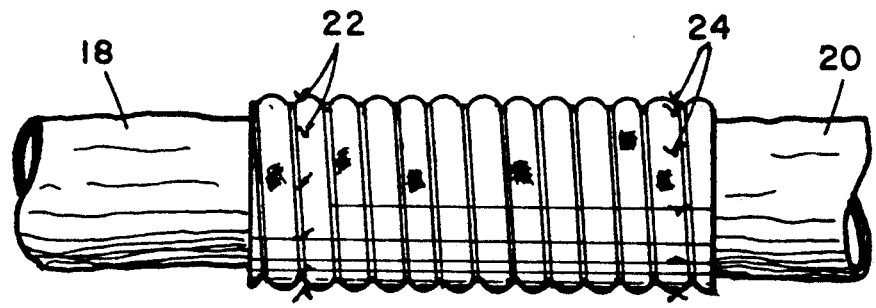
FIG. 2 is a side view of the crimped tube device shown with proximal and distal nerve ends affixed within the tube device in accordance with the present invention.
Figure 3:
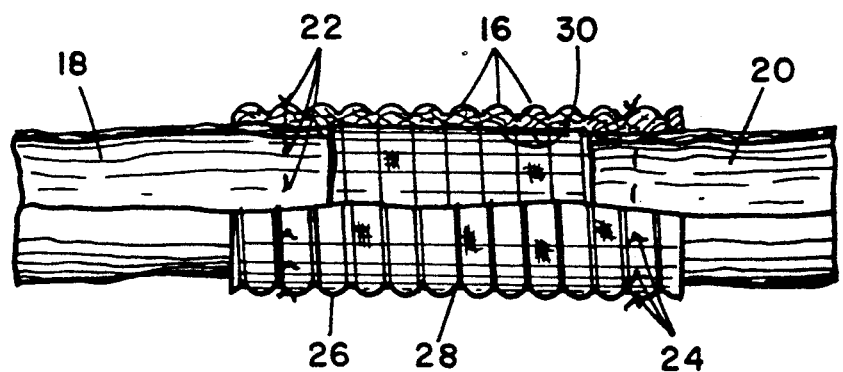
FIG. 3 is a partial cross-sectional view of the tube device shown in FIG. 2 showing the corrugated exterior surface in relation to the relatively smooth interior surface and having the proximal and distal nerve ends sutured in place within the tube device.

FIGS. 2 and 3 show the tube device 10 in place spanning a nerve gap or defect between a proximal nerve end 18 and a distal nerve end 20. A bioabsorbable suture material such as a DEXON ® (American Cyanamid Company, Wayne, N.J. 07470, USA) suture or a MAXON ™ (American Cyanamid Company, Wayne. N.J. 07470, USA) suture is shown at 22 and 24 connecting the proximal nerve end 18 and distal nerve end 20, to the wall of the tube device 10.

The suture 22 is threaded through the wall of the tube device at a point about 5 millimeters away from an end thereof and, then into the epineural layer of the proximal nerve end 18. The suture 22 is then pulled to bring the proximal nerve end into the end of the tube device 10. The suture 22 is tied to the wall of the tube in a manner that is known in the art. The process is then repeated with suture 24 to pull the distal nerve end 20 into the opposite end of the tube device.

As shown in FIG. 3, the proximal and distal nerve ends, 18 and 20 are secured within the tube device 10 such that a gap exists between the nerve ends. The proximal nerve end 18 will regenerate across the nerve gap into the distal nerve end 20. Referring to FIG. 3, the corrugations 16 are seen in more detail as comprising a series of ridges 26 and valleys 28 along the entire exterior tube surface 12. The interior surface 14 is shown to have a plurality of flats 30 to provide a relatively smooth surface to ease insertion of the nerve ends into the tube device and to provide an optimum environment for axonal growth within the tube. As shown in FIGS. 3 and 7, the internal diameter (D) of the tube device 10 is relatively constant due to the plurality of flats 30 provided therein.

Figure 4:
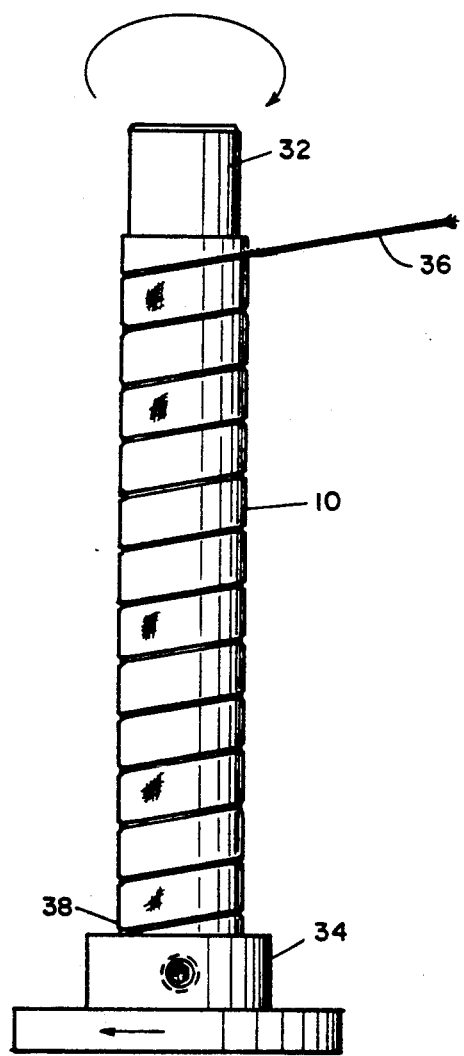
FIG. 4 is a side view of the fixture for crimping the tube including a steel rod and chuck with an uncrimped tube in place over the rod, a line of suture material being wrapped around the tube.
Figure 5:
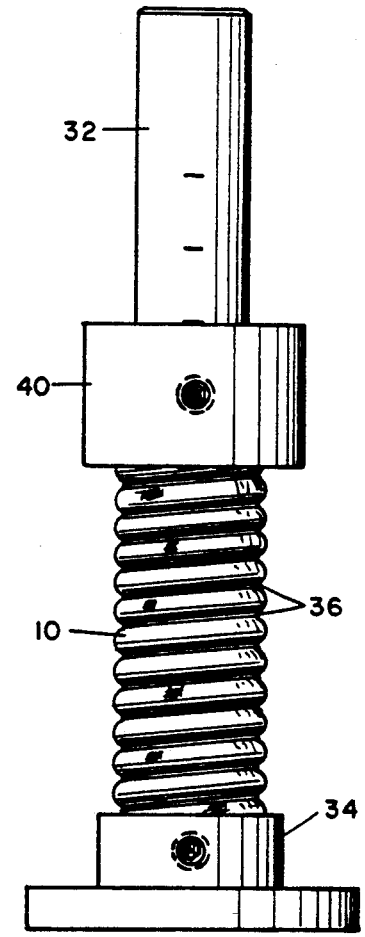
FIG. 5 is a side view of the crimping fixture showing the tube being longitudinally collapsed on the rod with a collar being placed adjacent each end of the tube to insure the tube holds the desired configuration.
Figure 6:
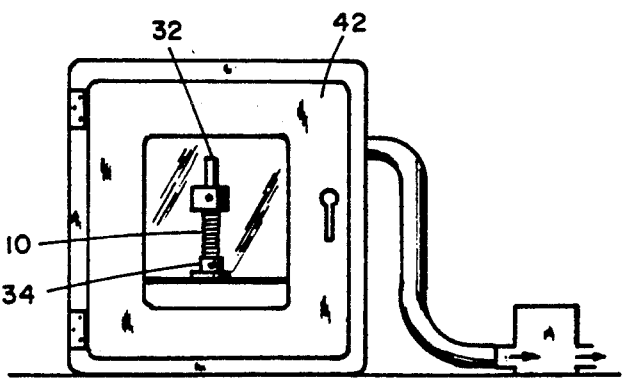

The manner of providing the corrugations 16 on the exterior tube surface 12 is shown in FIGS. 4-6. FIG. 4 shows an uncrimped mesh (knitted or woven) tube placed over a steel rod 32. The diameter of the rod 32 is appropriately sized so that the tube slides snugly over the rod. The rod 32 and mesh tube are mounted on a chuck 34 of a winding device such as a lathe (not shown) or other commercially available device to spin rod 32. A braider bobbin (not shown) is wound with a suture material 36 such as a 4/0 DEXON ® (American Cyanamid Company, Wayne, N.J. 07470, USA) suture material which can be mounted on the cutting tool holder (not shown) of the lathe. The suture material 36 is tied to one end of the tube as shown at 38 and then the lathe is rotated to wrap the suture material about the mesh tube 10. Preferably the suture material 36 is wound around mesh tube 10 such that there are approximately twelve (12) wraps of suture material per longitudinal inch of tube. When the total length of mesh tube has been wound with suture material the suture material 36 is cut and tied off around the opposite end of the mesh tube 10.

Referring to FIG. 5, the mesh tube 10 is shown collapsed or longitudinally compressed on the rod 32 so that the tubes overall length is cut approximately in half. A collar 40 is inserted on rod 32 to hold the mesh tube 10 in this collapsed or compressed condition. The compressed mesh tube 10, rod 32 and chuck 34 are then placed in a vacuum oven 42 as shown in FIG. 6. The vacuum oven is heated to 130° C. and a vacuum is pulled to less than or equal to 1 Torr. The mesh tube 10 is left in the vacuum oven at ≦ Torr and 130° C. for two hours. The use of a vacuum oven on the tube device also improves the in-vivo properties of the polymer fibers used to make up the tube device. The heat set process is more fully described in U.S. Pat. No. 3,422,181 to Chirgwin, Jr. and incorporated herein by reference.

The mesh tube 10, rod 32 and chuck 34 are removed from the vacuum oven 42 and cooled to room temperature in a Laminar Flow Hood (not shown). The suture material 36 is carefully removed leaving a crimped or corrugated mesh tube. The mesh tube 10 would then have both ends trimmed with scissors and be inserted into a thermoformed hinged tray. The tray is placed into a foil pouch for sterilization by known methods and sealed and sterilized a second time.

The tube device 10 shown in FIGS. 1-6 is knitted or woven from a plurality of bioabsorbable polymer fibers. The preferred polymers and copolymers are polyglycolic acid (U.S. Pat. No. 3,297,033), polyglycolic acid (U.S. Pat. No. 3,636,956) and poly(glycolic-co-trimethylene carbonate) (U.S. Pat. No. 4,243,775). These polymers and copolymers are preferred because they are known to be well tolerated by the body upon implantation in addition to being absorbable within the body.

The polymer and copolymer fibers are obtainable through methods known in the art. The fibers are then knitted or woven into tube shape. The various methods of knitting or weaving such mesh tubes are further described in the examples below.

In one embodiment of this invention the knitted or woven mesh tube is manufactured totally from polymer fibers of 100 percent PGA. The PGA material is a bioabsobable polymer which maintains its tensile strength for approximately thirty (30) days and is then slowly hydrolyzed within the body. Since the recognized neural growth rate is approximately one millimeter (1 mm) per day, a tube device manufactured from a PGA polymer fiber would remain in place about a severed nerve long enough to allow a nerve to regenerate across a 30 mm or 3 cm nerve gap or defect.

In another embodiment of this invention, the knitted or woven mesh tube is manufactured from a copolymer of glycolide and trimethylene carbonate linkages (MAXON ™ suture material). This copolymer fiber is known to maintain its tensile strength for at least fifty-six days before being slowly resorbed into the body. A tube device manufactured from the MAXON ™ copolymer fiber could be used to span nerve gaps of five centimeters or more.

Objects and advantages of this invention are further illustrated by the following examples, but the particular materials and amounts thereof recited in these examples, as well as other conditions and details, should not be construed to unduly limit this invention. For example, while the Examples disclose a yarn twist in the "Z" direction, the woven and knit tube constructions could use a twist in the "S" direction or a combination of fibers with yarn twists in both the "Z" and "S" directions could be combined in forming a tube product of the present invention.

EXAMPLE 1

Woven Tube Construction—PGA Polymer Fibers

PGA polymer fibers were woven on a single shuttle 1×1 Crompton & Knowles box loom using 16 harnesses. The mesh tube was woven as a double fabric with selvedge edges attached on both sides. The warp yarn was 3 ply, 46 denier/21 filament (fiber) PGA yarn having 5 turns per inch of twist in the "Z" direction.

The weft (filling) yarn was 3 ply, 46 denier/21 filament PGA yarn having 1.5 turns per inch of twist in the "Z" direction. The mesh tube construction was a 1×1 plain weave having 120 ends per inch per side and 88 picks per inch. The total number of ends in the mesh tube construction varied from approximately 60 to 111 to yield tube sizes of from 2 mm to 6 mm inside diameter (I.D.). The mesh tube was then crimped, heat set and cut to the desired length (6 cm) as discussed above. This construction yields a flexible and porous, woven mesh tube to be used in accordance with the present invention.

EXAMPLE 2

Woven Tube Construction—MAXON ™ Copolymer Fibers

MAXON ™ copolymer fibers were woven into a mesh tube on the same type of weaving loom as in Example 1. However, here the warp yarn was 5 ply, 50 denier/25 filament copolymer yarn having 5 turns per inch of twist in the "Z" direction. The weft (filling) yarn was 5 ply, 50 denier/25 filament copolymer yarn having 2 turns per inch of twist in the "Z" direction. The mesh tube construction was a 1×1 plain weave having 62 ends per inch per side and 68 picks per inch. The woven mesh tube was crimped and heat set as in Example 1 to provide a tube device in accordance with the present invention.

EXAMPLE 3

Knit Tube Construction—PGA Polymer Fibers

PGA polymer fibers were knit into a mesh tube on a tubular weft Lamb Knitting Machine using a single feed jersey stitch construction. The knitting machine cylinder had a needle density of 25 needles per inch and the total number of needles in a given cylinder were varied to yield a mesh tube diameter of from 2 mm to 6 mm I.D. after fabric finishing. The yarn used was formed by combining 4 plies of 46 denier/21 filament PGA fibers, all plied at 2.3 turns per inch of twist in the "Z" direction. The knitted mesh tubes were finished in the same manner as in Example 1 to provide a porous, flexible knitted mesh tube to be used in accordance with the present invention.

EXAMPLE 4

Knit Tube Construction—MAXON ™ Copolymer Fibers

MAXON ™ copolymer fibers were knit into a mesh tube on the same type of knitting maching and knit construction as in Example 3. However, the cylinder had a needle density of 33 needles per inch with a total needle count of about 14 about the perimeter. The yarn used was formed by combining 3 plies of 50 denier copolymer fibers and 1 ply of 25 denier copolymer fibers, all plied at 2.3 turns per inch of twist in the "Z" direction to yield a mesh tube diameter of about 2 mm I.D. after finishing. The knitted mesh tube was crimped and heat set as in Example 1, above.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method of promoting regrowth of a severed nerve across an extended nerve gap in excess of one centimeter, comprising the steps of:
   (a) providing a flexible and porous tube device manufactured from synthetic bioabsorbable polymer fibers;
   (b) inserting a proximal end of the severed nerve in a first end of the tube device;
   (c) inserting a distal end of the severed nerve in a second end of the tube device;
   (d) affixing the nerve ends within the tube device such that the proximal and distal ends of the severed nerve form a free space in excess of one centimeter depending on the length of missing nerve tissue; and
   (e) allowing new nerve tissue to grow across to free space.

2. The method according to claim 1 wherein the proximal and distal nerve ends are pulled into the first and second ends of the tube by the steps of:
   (a) passing a suture through the tube wall at about a five millimeter distance from each end of the tube and, then, into the epineural layer of the respective proximal and distal nerve ends;
   (b) pulling said suture such that the respective nerve ends are pulled into each end of the tube; and
   (c) affixing the suture about the tube so that the nerve ends remain in a fixed position within the tube such that the proximal and distal nerve ends are spaced at a predetermined distance from each other.

3. The method according to claim 1 wherein a tube is provided having a corrugated exterior surface such that said tube can be bent through an arc of up to 180 degrees without crimping the internal surface of said tube and a relatively smooth internal surface to help promote longitudinal axon growth across the nerve gap within the tube.

4. The method according to claim 3 wherein the tube is knitted or woven from a plurality of bioabsorbable polymer fibers selected from the group consisting of polyglycolic acid, polylactic acid, polydioxanone, poly(lactide-co-glycolide), poly(glycolide-co-trimethylene carbonate), polyestermides, and copolymers and mixtures thereof.

5. The method according to claim 4 wherein the knitted or woven tube is subjected to heat treatment in a vacuum box to heat set the knitted or woven fibers.

6. The method according to claim 4 wherein a corrugated tube is provided by using bioabsorbable polymer fibers of polyglycolic acid, and the proximal and distal nerve ends are affixed within the tube such that the nerve ends are spaced up to 3 centimeters from each other.

7. The method according to claim 4 wherein a corrugated tube is provided by using bioabsorbable polymer fibers which are poly(glycolide-co-trimethylene carbonate), and the proximal and distal nerve ends are affixed within the tube such that the nerve ends are spaced up to 6 centimeters from each other.

8. The method of claim 3 wherein the nerve gap is from about 2 millimeters to about 2 centimeters.

9. The method of claim 3 wherein the nerve gap is at least about 2 centimeters.

10. The method of claim 1 wherein the nerve gap is at least about 1.5 centimeters.

11. The method of claim 1 wherein the nerve gap is at least about 2 centimeters.

12. A method of promoting regrowth of a severed nerve across an extended nerve gap in excess of one centimeter comprising the steps of:
 (a) providing a flexible and porous tue device manufactured form synthetic bioabsorbable polymer fibers, said tube device having a plurality of corrugations on its exterior surface positioned so as to allow said tube to be bent without crimping the internal surface of said tube and having a internal surface to promote longitudinal axon growth across the nerve gap;
 (b) inserting a proximal end of the severed nerve in a fit end of the tube device;
 (c) inserting a distal end to the severed nerve in a second and of the tube device;
 (d) affixing the nerve ends within the tube device; such that the proximal and distal ends of the severed nerve form a free space in excess of one centimeter depending on the length of missing nerve tissue and
 (e) allowing new nerve tissue to grow across the free space.

13. The method according to claim 12 wherein a tube device is provided having a plurality of flats on its internal surface to provide a substantially constant internal diameter to promote longitudinal axon growth within the tube device and across the nerve gap.

14. A method of promoting regrowth of a severed nerve across an extended nerve gap in excess of one centimeter comprising the steps of:
 (a) providing a flexible and porous tube device having a lumen and manufactured from synthetic bioabsobable polymeric material;
 (b) inserting a proximal end of the severed nerve in the lumen at a first end of the tube device;
 (c) inserting a distal end of the servered nerve in the lumen at a second end of the tube device;
 (d) affixing the nerve ends within the tube device such that a gap exists within the lumen between the nerve ends which enables nerve growth to close the gap, the proximal and distal ends to the servered nerve are at a preselected distance forming a free space in excess of one centimeter depending on the length of missing nerve tissue; and
 (e) allowing new nerve tissue to grow across the free space.

15. The method according to claim 14 wherein said step of providing a tube includes providing the tube with a relatively smooth internal surface defining the lumen to help promote longitudinal axon growth across the nerve gap.

* * * * *